United States Patent
Lin et al.

(10) Patent No.: US 12,336,852 B2
(45) Date of Patent: Jun. 24, 2025

(54) METHODS FOR GENERATING SKELETAL CHARACTERISTIC VALUES RELATED TO BONE QUALITY

(71) Applicant: Alpha Intelligence Manifolds, Inc., New Taipei (TW)

(72) Inventors: Chia-Hung Lin, New Taipei (TW); Win-How Lee, New Taipei (TW)

(73) Assignee: ALPHA INTELLIGENCE MANIFOLDS, INC., New Taipei (TW)

(*) Notice: Subject to any disclaimer, the term of this patent is extended or adjusted under 35 U.S.C. 154(b) by 230 days.

(21) Appl. No.: 17/814,501

(22) Filed: Jul. 22, 2022

(65) Prior Publication Data
US 2023/0029674 A1 Feb. 2, 2023

(30) Foreign Application Priority Data
Jul. 22, 2021 (TW) .................. 110127047

(51) Int. Cl.
| | |
|---|---|
| A61B 6/50 | (2024.01) |
| A61B 5/00 | (2006.01) |
| A61B 6/00 | (2006.01) |
| A61B 6/46 | (2024.01) |

(52) U.S. Cl.
CPC ............ *A61B 6/505* (2013.01); *A61B 5/4509* (2013.01); *A61B 6/469* (2013.01); *A61B 6/5217* (2013.01)

(58) Field of Classification Search
CPC ....... A61B 6/505; A61B 5/4509; A61B 6/469; A61B 6/5217
See application file for complete search history.

(56) References Cited

U.S. PATENT DOCUMENTS

| | | | | | |
|---|---|---|---|---|---|
| 5,365,564 | A | * | 11/1994 | Yashida | A61B 6/583 378/55 |
| 5,594,775 | A | * | 1/1997 | Hangartner | A61B 6/583 378/207 |
| 2003/0063704 | A1 | * | 4/2003 | Lang | G01N 23/04 378/54 |

(Continued)

FOREIGN PATENT DOCUMENTS

| | | |
|---|---|---|
| CN | 103892856 A | 7/2014 |
| CN | 104363832 A | 2/2015 |

(Continued)

OTHER PUBLICATIONS

Behrooz et al., "Automated Quantitative Bone Analysis in In Vivo X-ray Micro-Computed Tomography", IEEE Transaction on Medical Imaging, vol. 36, No. 9, pp. 195 (Year: 2017).*

(Continued)

*Primary Examiner* — Kiho Kim
(74) *Attorney, Agent, or Firm* — Huan-Yi Lin

(57) ABSTRACT

The present invention relates to a method of generating one or more skeletal characteristic values of a subject from a planar bone image, comprising identifying one or more regions of interest (ROIs) in the planar bone image and performing one or more feature analyses on the regions of interest to generate the skeletal characteristic values. The generated characteristic values correspond to the bone quality of the subject, and may be used to evaluate the overall bone status and future fracture risk.

42 Claims, 14 Drawing Sheets

(56) References Cited

U.S. PATENT DOCUMENTS

| | | | | |
|---|---|---|---|---|
| 2003/0198316 A1* | 10/2003 | Dewaele | ............... | G16H 15/00 |
| | | | | 378/54 |
| 2005/0015002 A1* | 1/2005 | Dixon | ................. | A61B 5/1038 |
| | | | | 600/595 |
| 2017/0098315 A1* | 4/2017 | Hara | ................... | A61B 6/5211 |

FOREIGN PATENT DOCUMENTS

| | | | | | |
|---|---|---|---|---|---|
| CN | 108174293 | A | * | 6/2018 | ......... G06K 9/00302 |
| CN | 108778418 | A | | 11/2018 | |
| CN | 112529863 | A | | 3/2021 | |
| CN | 113017657 | A | | 6/2021 | |
| JP | 2014056442 | A | * | 3/2014 | |
| KR | 20200085470 | A | * | 7/2020 | |

OTHER PUBLICATIONS

Zhou et al., "Automatic Detection and Classification of Rib Fractures on Thoracic CT Using Convolutional Neural Network: Accuracy and Feasibility", Thoracic Imaging, Jorean Journal of Radiology, pp. 869-879. (Year: 2020).*

* cited by examiner

METHODS FOR GENERATING SKELETAL CHARACTERISTIC VALUES RELATED TO BONE QUALITY

RELATED APPLICATION

This application claims the benefit of the Taiwan Patent Application No. 110127047 filed on Jul. 22, 2021, titled "BONE CHARACTERISTIC VALUE ESTIMATION METHOD," which is incorporated herein by reference at its entirety.

BACKGROUND OF THE INVENTION

Field of the Invention

The present invention relates to a method for generating skeletal characteristic values from a planar bone image, especially the skeletal characteristic values related to osteoporosis and fracture risk of a subject.

Description of Related Art

In the past few decades, the incidence of osteoporosis has gradually increased as aging society being a mega trend in the world. According to the definition of the World Health Organization (WHO), osteoporosis is a systemic bone disease characterized by decreased bone mass and deterioration of the microstructure of bone tissue, resulting in fragile bones and an increased risk of fracture. In addition to the increased risk of fractures, patients may also have multiple complications following fractures. Osteoporosis has thus become an important medical and public health issue.

Since osteoporosis is usually painless and has no obvious symptoms, one must take examinations to know whether he/she has osteoporosis or not. The diagnosis of osteoporosis can be made using conventional radiography and by measuring the bone mineral density (BMD), where the standard method of measuring BMD is dual-energy X-ray absorptiometry (DXA). The principle of DXA is to use two different energies of X-rays to irradiate the examination site, and measure the BMD value (unit: $g/cm^2$) according to different energy absorption. Nevertheless, a DXA scanner is expensive with only single function of measuring BMD, and thus DXA scanners are difficult to popularize to local hospitals and clinics due to cost-effectiveness considerations.

Except bone density, there are also other factors influence the strength of a bone and the risk of bone fracture. For example, the bending strength of bones is influenced not only by the amount of bone, but also by its geometrical distribution. In cortical bone, mechanical strength is affected by the histological structure, including the presence of primary versus osteonal bone, the orientation of the collagen fibers, the number and orientation of the cement lines, and the presence of microdamage. In cancellous bone, mechanical strength is affected by the microstructural arrangement of the trabeculae, including their orientation, connectivity, thickness, and numbers. Despite the importance of the above-mentioned factors, they are hard to well-evaluated by bone density measurement.

Therefore, it is desirable to develop a new method to evaluate the risk of bone fracture more conveniently and accurately.

SUMMARY OF THE INVENTION

To resolve the problems, the present invention provides a method to accurately estimate the bone mineral density (BMD) of a subject from an already obtained X-ray planar image, without the requirement of taking dual-energy X-ray absorptiometry (DXA) measurements. The present invention also provides a mean to analyze the structural and textural features of the X-ray planar image, which is not available in DXA measurements.

The method disclosed herein comprises the steps of identifying one or more regions of interest (ROIs) in the planar bone image and performing one or more feature analyses on the regions of interest to generate the skeletal characteristic values (SCVs) comprising either a plurality of density SCVs or at least one texture SCV. The method is characterized in that the feature analyses comprise either (1) a density analysis on one of the ROIs to generate the plurality of density SCVs related to bone density, or (2) a texture analysis on at least one of the ROIs to generate the texture SCV indicating the size distribution of the pores in the bone of the planar bone image.

In one embodiment, before identifying the ROIs a background removal mean is applied, and the method further comprises removing an interfering image caused by non-skeletal objects from the planar bone image.

In one embodiment, the skeletal characteristic values are further used to determine one or more bone status of the subject. The bone status may include osteoporosis status, fracture risk in the future, and any other bone-quality related evaluations.

In one embodiment, the skeletal characteristic values (SCVs) are bone mineral density (BMD) of different positions generated by the density analysis. The different position may contain total hip joint, femoral neck, greater trochanter and femoral shaft, which are the same as the BMD values measured by traditional DXA.

In one embodiment, the texture analysis comprises a local binary patterns (LBP) method and a region growing method.

In one embodiment, the region growing method is performed by calculating the number of pores with different porous sizes in an LBP processed ROI.

In one embodiment, the feature analyses further comprise a width analysis to obtain one or more width information of the bones in the ROIs. The width analysis may be performed by measuring the cortical width and the endosteal width of the lesser trochanter in the ROI, and the measured width information may be used to calculate cortical thickness index (CTI).

In one embodiment, a plurality of non-image features is introduced for bone status evaluation, and the bone status is determined by the skeletal characteristic values and the plurality of non-image features. The non-image features may be age, weight, height, gender, or any other factors influence bone quality of the subject. In one specific embodiment, the bone status is the Fracture Risk Assessment Tool (FRAX) score calculated by the generated skeletal characteristic values and the non-image features.

Other objectives, advantages and novel features of the invention will become more apparent from the following detailed description when taken in conjunction with the accompanying drawings.

DETAILED DESCRIPTION OF PREFERRED EMBODIMENTS

The terminology used in the description presented below is intended to be interpreted in its broadest reasonable manner, even though it is used in conjunction with a detailed description of certain specific embodiments of the technology. Certain terms may even be emphasized below; however, any terminology intended to be interpreted in any restricted manner will be specifically defined as such in this Detailed Description section.

The embodiments introduced below can be implemented by programmable circuitry programmed or configured by software and/or firmware, or entirely by special-purpose circuitry, or in a combination of such forms. Such special-purpose circuitry (if any) can be in the form of, for example, one or more application-specific integrated circuits (ASICs), programmable logic devices (PLDs), field-programmable gate arrays (FPGAs), graphics processing units (GPUs), etc.

Figure 1:
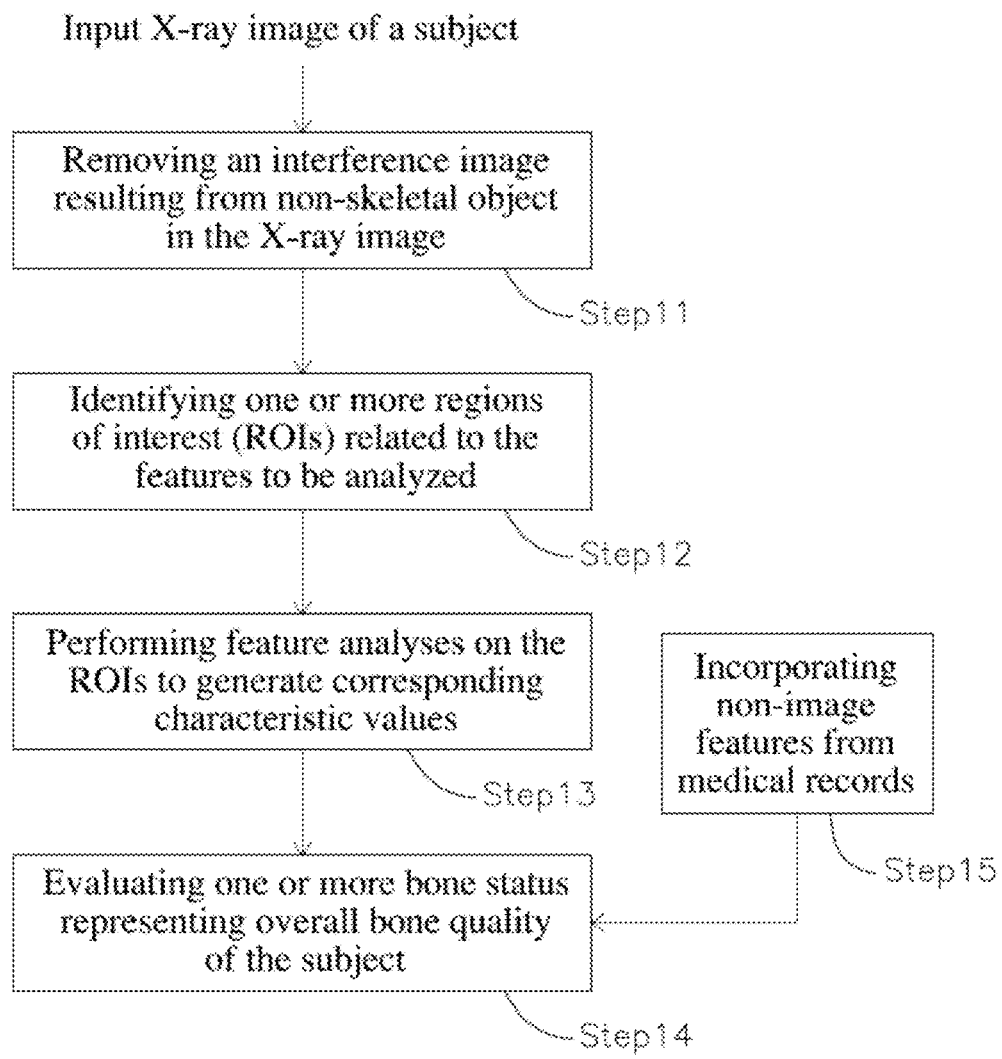
FIG. 1 is the block diagram of a preferred embodiment of the method generating skeletal characteristic values and evaluating bone status in the present application.

In the present application, a method for generating characteristic values of multiple bone features is provided, where the characteristic values can be subsequently used to evaluate the bone status and the risk of bone fractures. A flowchart of the method is shown in FIG. 1. The embodiments implementing only step 12 and 13 will bring satisfactory results, and the embodiments implementing all steps from step 11 to step 15 are preferred embodiments.

As shown in FIG. 1, step 11 may be applied to an obtained X-ray planar image to remove an interference image caused by non-skeletal objects in the X-ray planar image. Most of the non-skeletal objects are soft tissues (such as human muscles) or non-human tissues (such as clothing or surgical implants), which may interfere with the generation of skeletal characteristic values. The method for removing the interfering images caused by non-skeletal objects may be an existing image processing method (e.g., an image background removal algorithm), which automatically removes the images generated by the non-skeletal objects, so as to generate a cleaner skeletal image. The interference image removal method (e.g., the image background removal algorithm) may also be trained by an artificial intelligence technology to increase its accuracy. An example of background removal is provided in Example 1 below.

Once the X-ray image is taken and optionally undergoes interference image removal, one or more regions of interest (ROIs) can be manually and/or automatically located, as shown in step 12. The location and size of the ROI may be marked manually, marked automatically using software algorithms, or even marked semi-automatically by user a-priori input as the seed for software automatic placement or post processing manual adjustment. In preferred embodiments of the present invention, an object detection artificial intelligence (AI) is used to automatically locate the regions of interest (ROIs). The AI detection model may be regular object detection deep neural network (DNN) models, such as You Only Look Once (YOLO), Single Shot MultiBox Detector (SSD), and RetinaNet algorithms. The AI may be trained by a data set labeled by experts, which represents the training ground truth for the object detection model. The trained AI is then able to identify the ROIs with the features to be analyzed to generate the corresponding skeletal characteristic values. In some embodiments, the AI may be trained to identify multiple sets of ROIs corresponding to multiple features related to the bone quality of a subject, which will be described below. An example of ROI identification is provided in Example 2.

Figure 2A:
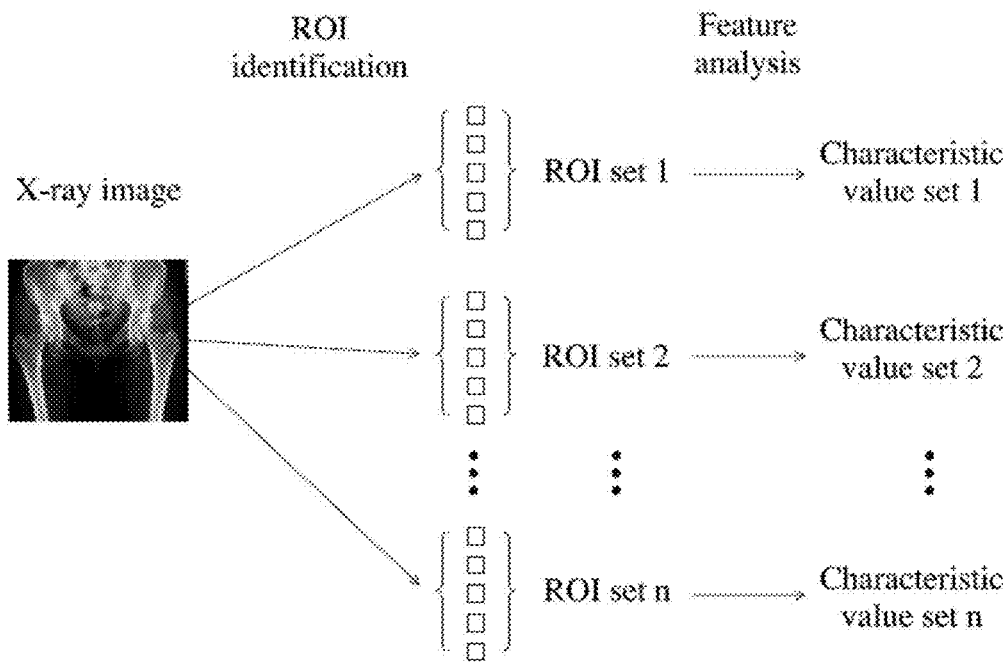
FIG. 2A shows an embodiment of ROI identification where different sets of ROIs are identified and located independently.
Figure 2B:
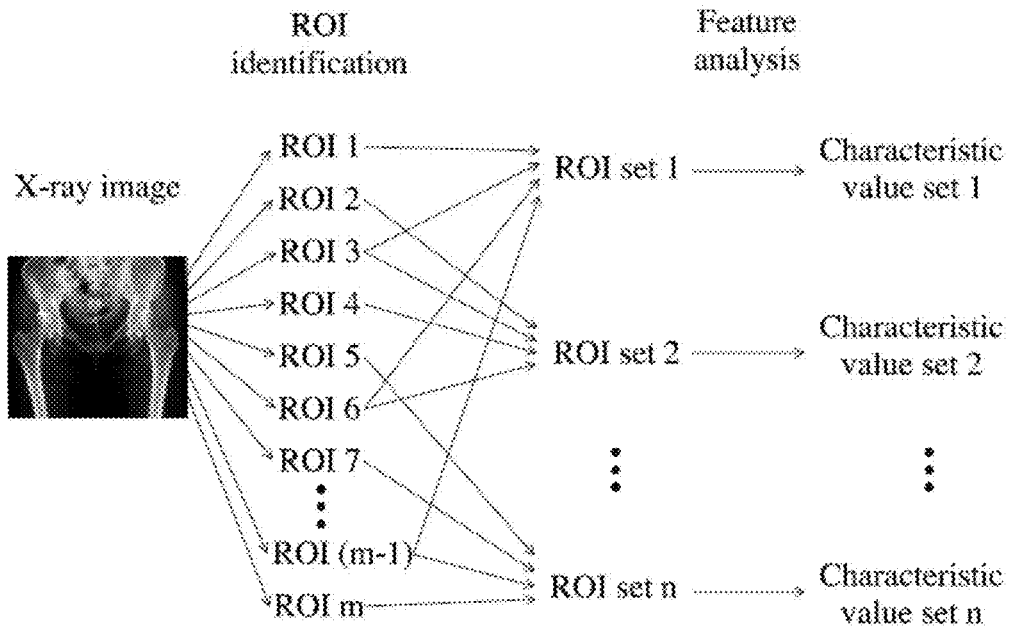
FIG. 2B shows an embodiment of ROI identification where all ROIs are identified and located together.

After ROI identification, step 13 is applied to perform one or more feature analyses to the ROIs to the generated skeletal characteristic values. The bone features to be analyzed are the factors which influence the bone strength and the risk of bone fracture. Some examples of the features include but are not limited to bone density, cortical thickness, trabecular structure, specific angles of the bones, porous size of the bones, and length of the bones. The skeletal characteristic values are the measurements of the features related to the bone quality, some of which are regularly used to diagnose osteoporosis and evaluate the risk level of bone fracture of a subject. Examples of characteristic values include but are not limited to bone mineral density (BMD), cortical thickness index (CTI) and trabecular bone score (TBS). Some features and characteristic values which are not conventionally used may also be analyzed, such as measuring the number of pores with different porous size in the X-ray image to evaluate the trabecular structure of bones. The characteristic values obtained by feature analyses may be subsequently used to determine the bone status, as shown in step 14. As described earlier, there may be different factors related to bone fragility and therefore different features related to bone fractures. To obtain multiple sets of characteristic values corresponding to different features, multiple sets of ROIs for different features may be generated based on the features to be analyzed. For example, an input X-ray radiograph may be used to estimate the BMD values, CTI values and TBS of the bone in the image, which requires one set of ROIs for each feature to be analyzed. Different sets of ROIs may be identified and/or located independently, as shown in FIG. 2A; alternatively, all ROIs may also be identified together, as shown in FIG. 2B. Therefore, an ROI may only be used in one feature analysis, or it may be used in more than one feature analyses. With the identified ROIs, the skeletal characteristic values can be generated by programmable software based on the image patterns of the ROIs. The image patterns, which includes but are not limited to brightness, contrast, shape, porous size, and distance, can be extracted and analyzed by an established algorithm or a trained AI. The desired characteristic values can then be generated with the extracted patterns by the established algorithm or the trained AI. The number of required ROIs in a feature analysis is determined based on the logic of feature analysis, and is not correlated to the number of characteristic values generated. A feature analysis method may use one ROI to generate several characteristic values. On the other hand, a feature analysis may also use several ROIs to generate a characteristic value. The AI training algorithms for feature analysis include but are not limited to linear regression, support vector machine (SVM), XG-Boost (eXtreme Gradient Boosting) and deep neural network (DNN). The obtained characteristic values, as such BMD and CTI, may indicate the status of bones from different perspective, some of which may have a close correlation with osteoporosis. Examples of generating different characteristic values are provided in Example 3-Example 5 below.

In step 14, an overall bone status may further be generated based on the skeletal characteristic values. The bone status represents the final evaluation of the bone quality of the subject. The final evaluation may be an integrated result (e.g. a score) of bone strength, a predicted risk of fracture, or a diagnosed osteoporosis status. Since some health conditions are not available from the X-ray image, some non-image features from medical records may also be incorporate into the evaluation of bone status, as shown in step 15. Those non-image features include but are not limited to age, weight, height, gender, smoking habit, alcohol use, and existence of previous fractures of the subject. The Fracture Risk Assessment Tool (FRAX) provides an example of integrating image features and non-image features to evaluate total fracture risk within 10 years.

EXAMPLES

The following examples are provided to further illustrate the image processing method as claimed.

1. Interference Image Removal

An X-ray two dimensional images obtained by a normal X-ray machine undergoes interference image removal. The first step of interference image removal utilizes a U-net neural network to segment the bone area of the input image. The U-net is a well-known convolutional neural network architecture, which is trained in advance by a training model using a bone data collection with labeling.

The second step of interference image removal takes the pixel values around the bone contour, predict soft tissue values over the region by solving a Laplace equation and then subtract the soft tissue values from the input image, as described by Gong in journal article titled "Decompose X-ray Images for Bone and Soft Tissue" (arXiv: 2007.14510v1). In brief, with the input X-ray image f(x, y), obtain the mask M(x, y) by active contour or user input, then compute the soft tissue interference image S(x, y) by solving the equation below:

$$\Delta S_M = 0, \text{s.t.} \ S_{\partial M} = f_{\partial M}, \quad \text{(Eq. 1)}$$

where $\partial$ denotes the boundary. After calculating S(x, y), compute a value by the following equation:

$$\alpha \equiv \frac{1}{\max\left\{\frac{f(x, y) - S(x, y)}{1 - S(x, y)}\right\}} \quad \text{(Eq. 2)}$$

Lastly, compute the soft tissue interference image removed bone image U(x, y) by the equation below:

$$U(x, y) = \alpha \frac{f(x, y) - S(x, y)}{1 - S(x, y)} \quad \text{(Eq. 3)}$$

The U(x, y) described in Eq. 3 is the desired bone image with interference image removed.

Figure 3A:
FIG. 3A shows the original X-ray image before interference image removal.
Figure 3B:
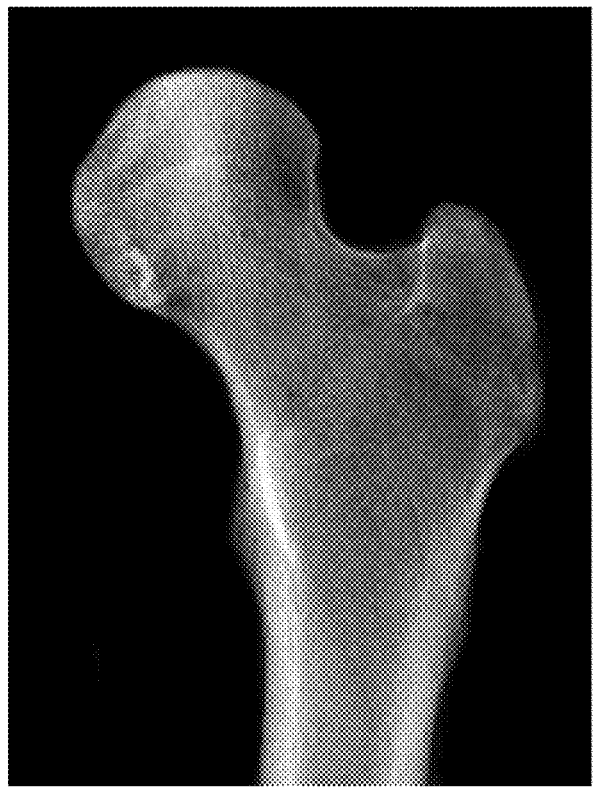
FIG. 3B shows the X-ray image after interference image removal.

The U-net neural network may also be trained to segment the bone area of the desired bones and eliminate unwanted bones, as shown in FIGS. 3A and 3B. The interference image removed X-ray radiograph contains the bone area of femur only.

2. ROI Location

Figure 4A:
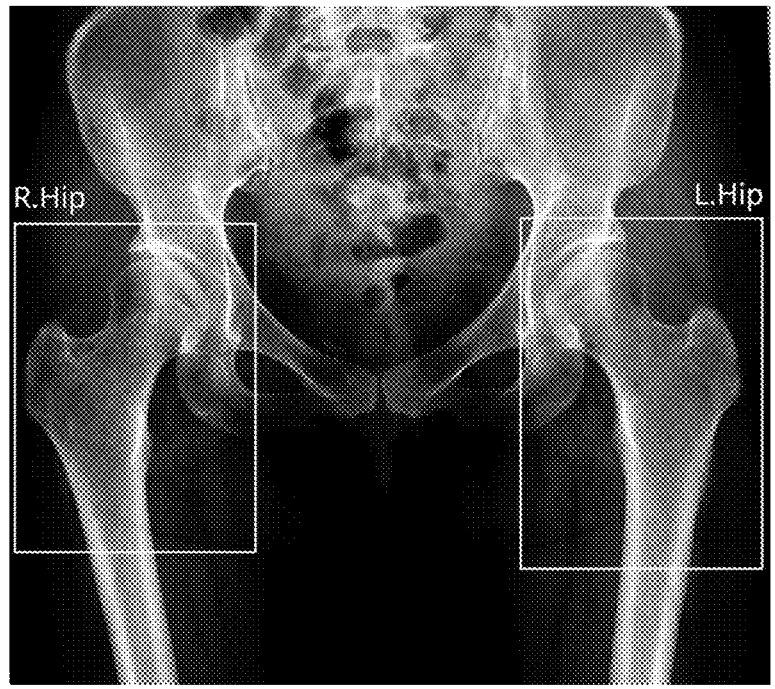
FIG. 4A shows a training image of total hip with left and right hip joint labeled by a radiologist.
Figure 4B:
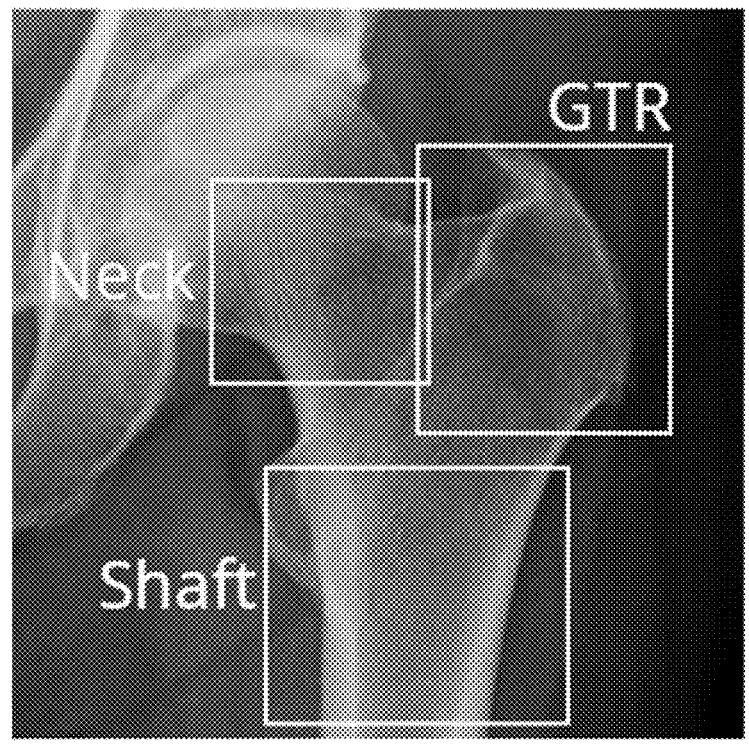
FIG. 4B shows a training image of hip joint region with femoral neck, greater trochanter and femoral shaft labeled by a radiologist.

An AI detection model is trained to identify regions of interest (ROIs) to be analyzed in the image. A deep neural network (DNN) model, You Only Look Once (YOLO) algorithm, is implemented to train the AI to identify the features and select suitable ROIs from the input image. The training dataset and training workflow for BMD generation are as described below:

(1) In the training dataset, the ROIs in the X-ray images are labeled by experts as the training ground truth for the object detection model. Clinical data of 459 Pelvis X-ray images from health facilities are transformed from DICOM files into high-resolution 16-bit PNG files. The images with abnormal bones such as artificial joints or fractures are excluded. The brightness and contrast of the images are then adjusted to a standard range. Lastly, regions of hip joint, femoral neck, greater trochanter and femoral shaft are labeled by radiologists as the training ground truth, as shown in FIGS. 4A and 4B.

(2) The labeled ROIs (the bounding boxes in FIGS. 4A and 4B) and the unlabeled corresponding X-ray images are used to train the object detection model implementing YOLO algorithm.

(3) After training, the model is able to locate ROIs in the incoming hip X-ray images. The ROI of hip joint region is located from the whole X-ray image, and the ROIs of femoral neck, greater trochanter and femoral shaft are located from the ROI of hip joint region.

Figure 5A:
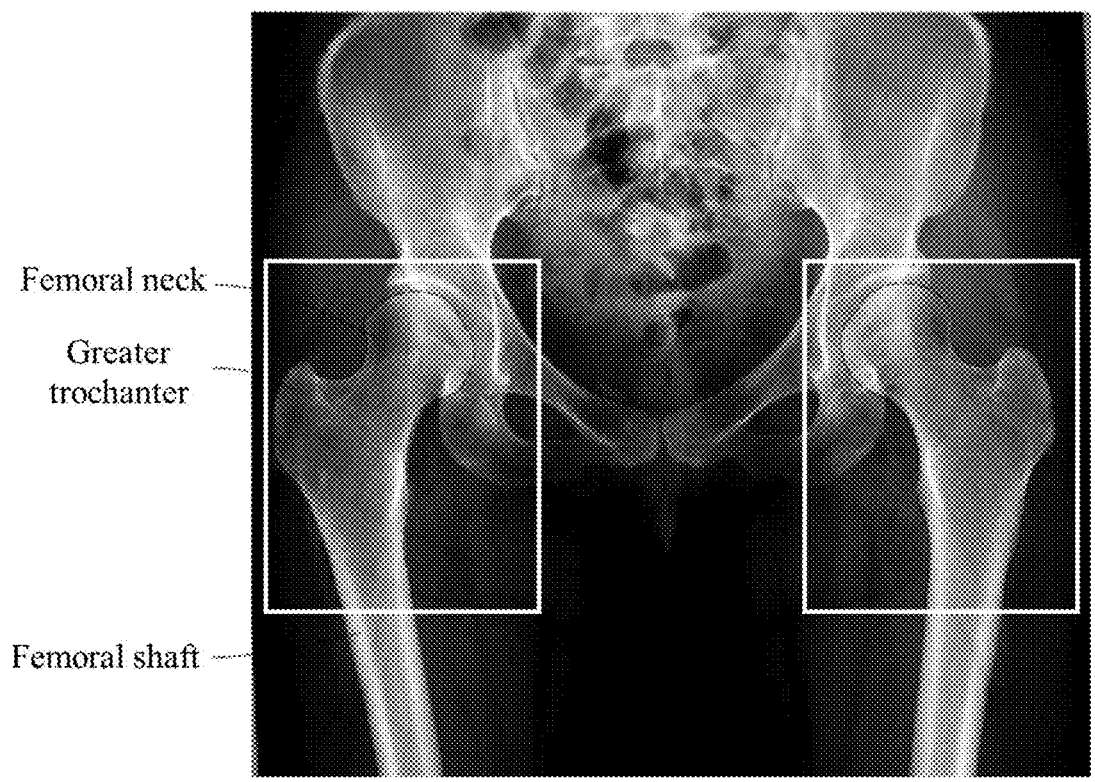
FIG. 5A is the results of ROI identification for BMD generation, which identifies hip joint regions as regions of interest.

FIG. 5A is the results of ROI identification for BMD generation, which selects hip joint regions as regions of interest. The result shows a good recognizing ability to identify correct ROIs. The hip joint region is the only ROI required in BMD generation.

3. BMD Generation

Figure 6A:
FIG. 6A shows an input X-ray image for BMD generation.
Figure 6B:
FIG. 6B shows the ROI identified by the AI model.

An AI model implementing a ResNet algorithm (ResNet50) is trained to generate the bone mineral density (BMD) from an input X-ray image. Clinical data of 1332 X-ray images with corresponding DXA measurement from health facilities are transformed from DICOM files into high-resolution 16-bit PNG files. The images with abnormal bones such as artificial joints or fractures are excluded. The brightness and contrast of the images are then adjusted to a standard range. For each X-ray image, the corresponding DXA report with BMD values of 4 regions (total hip joint, femoral neck, greater trochanter and femoral shaft) are matched to the X-ray image. Only the matches where the time interval between the X-ray radiograph and DXA measurement less than 6 months are included as training data. The DXA measurements of the training data contain BMD values of total hip, femoral neck, greater trochanter and femoral shaft for each X-ray training image. The learning model for BMD generation implements the ROI location model trained before and is able to identify the required regions automatically for BMD generation. Therefore, the training ground truth only contain the X-ray images with corresponding BMD values, and the ROIs of the hip joint region. Other regions (femoral neck, greater trochanter and femoral shaft) with labels are not required as the ground truth. The model is trained to generate the BMD values of all 4 regions (total hip, femoral neck, greater trochanter, and femoral shaft) simultaneously, instead of being trained to generate the BMD values independently. The model converges after 200 epochs. The trained model is then used to generate the BMD values of bones in the input X-ray image. An example for BMD generation is provided here. A pelvis X-ray as shown in FIG. 6A is used as the input, and the hip joint region is identified as hip joint ROI, as shown in FIG. 6B. The generation results for BMD values are provided in Table 1.

TABLE 1

The generated and DXA measured BMD values for the input X-ray image

| Region | Femoral neck | Greater trochanter | Femoral shaft | Total hip |
|---|---|---|---|---|
| Generated BMD values | 0.9005109 | 0.774951 | 1.250777 | 0.99626714 |
| DXA measured BMD values | 0.9288374 | 0.8845116 | 1.3530874 | 1.085378 |

Figure 7A:
FIG. 7A shows the Grad-CAM outputs for the DNN model generating BMD value of femoral neck.
Figure 7B:
FIG. 7B shows the Grad-CAM outputs for the DNN model generating BMD value of greater trochanter.
Figure 7C:
FIG. 7C shows the Grad-CAM outputs for the DNN model generating BMD value of femoral shaft.
Figure 8A:
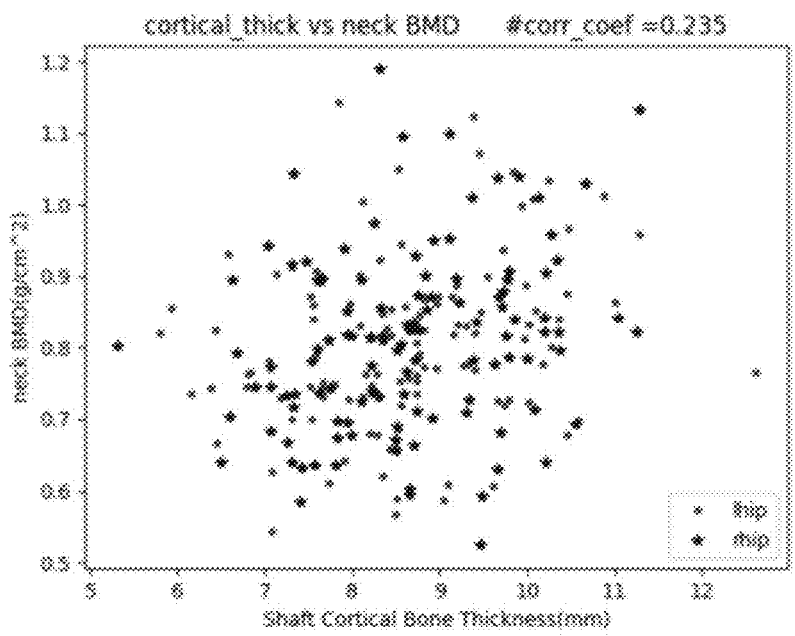
FIG. 8A shows the correlation between the cortical bone thickness of femoral shaft and the BMD value of femoral neck.
Figure 8B:
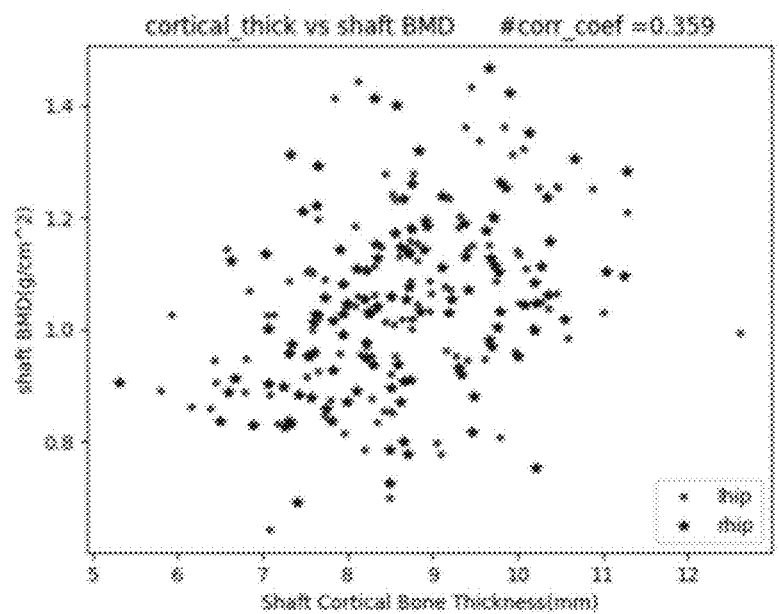
FIG. 8B shows the correlation between the cortical bone thickness of femoral shaft and the BMD value of femoral shaft.
Figure 8C:
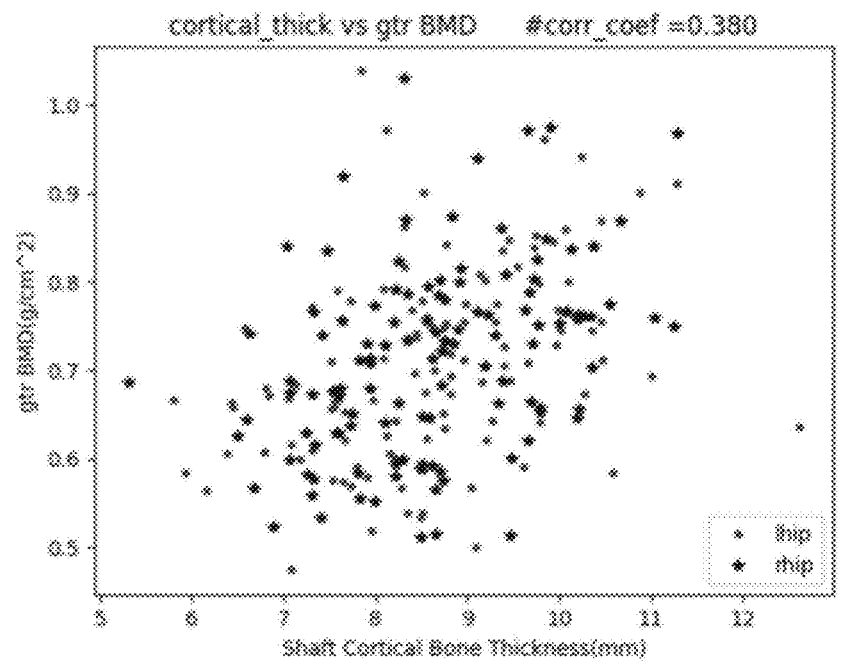
FIG. 8C shows the correlation between the cortical bone thickness of femoral shaft and the BMD value of greater trochanter.
Figure 8D:
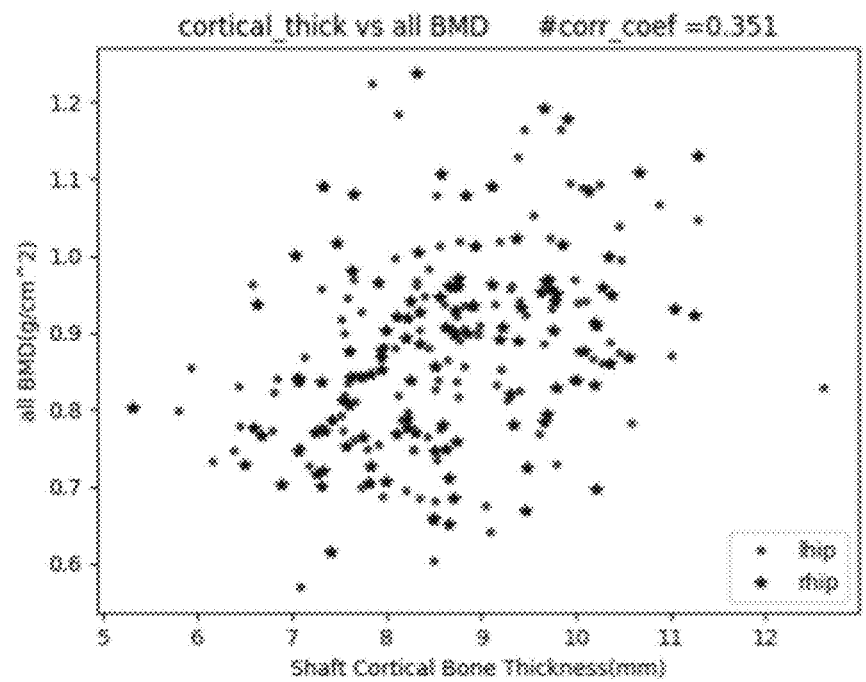
FIG. 8D shows the correlation between the cortical bone thickness of femoral shaft and the BMD value of the total hip region.

The trained model is also tested by Gradient-weighted Class Activation Mapping (Grad-CAM) to compute the importance map for each region, as shown in FIG. 7A-7C. The result indicates that the DNN model indeed generates BMD based on the ROI of femoral neck (FIG. 7A), greater trochanter (FIG. 7B) and femoral shaft (FIG. 7C).

The result above shows a good consistency between the generated BMD values and the corresponding true values. The accuracy of the trained model is further verified with 489 cases as test data, as shown in Table 2, where the generation results for model trained to generate only 1 region (femoral neck) are also provided for comparison.

TABLE 2

The comparison of models generating 1 ROI vs 4 ROIs (*1)

| | AUC of ROC (*2) | Accuracy (*3) | Neck BMD RMSE (*4) |
|---|---|---|---|
| model trained to generate only the neck ROI | 0.9187 | 0.840 | 0.0652 |
| model trained to generate 4 ROIs simultaneously | 0.922 | 0.845 | 0.0601 |

(*1): The ROC, accuracy and RMSE of 4 ROI are calculated for femoral neck only.
(*2): AUC (area under the Curve) of ROC (receiver operating characteristic curve) is calculated from the generating result of osteoporosis/non-osteoporosis classification (best = 1, worst = 0.5).
(*3): Accuracy is the ratio of correctly classified cases for osteoporosis/non-osteoporosis classification.
(*4): RMSE is the root mean squared error between the generated neck BMD and the true BMD values.

Table 2 shows that generating the BMD values for all 4 regions (total hip, femoral neck, greater trochanter, and femoral shaft) simultaneously leads to a smaller (and thus an improved) RMSE value compared to generating 1 region only. Although the AUC and accuracy of evaluating osteoporosis perform similarly well between two models, the osteoporosis/non-osteoporosis classification only represents true-false evaluation of the bone status. However, a significantly better RMSE value represent an improved prediction ability in numerical BMD value, which provides more insight into the total bone quality of a subject, compared to the much simpler osteoporosis/non-osteoporosis classification.

4. CTI Measurement

Figure 5B:
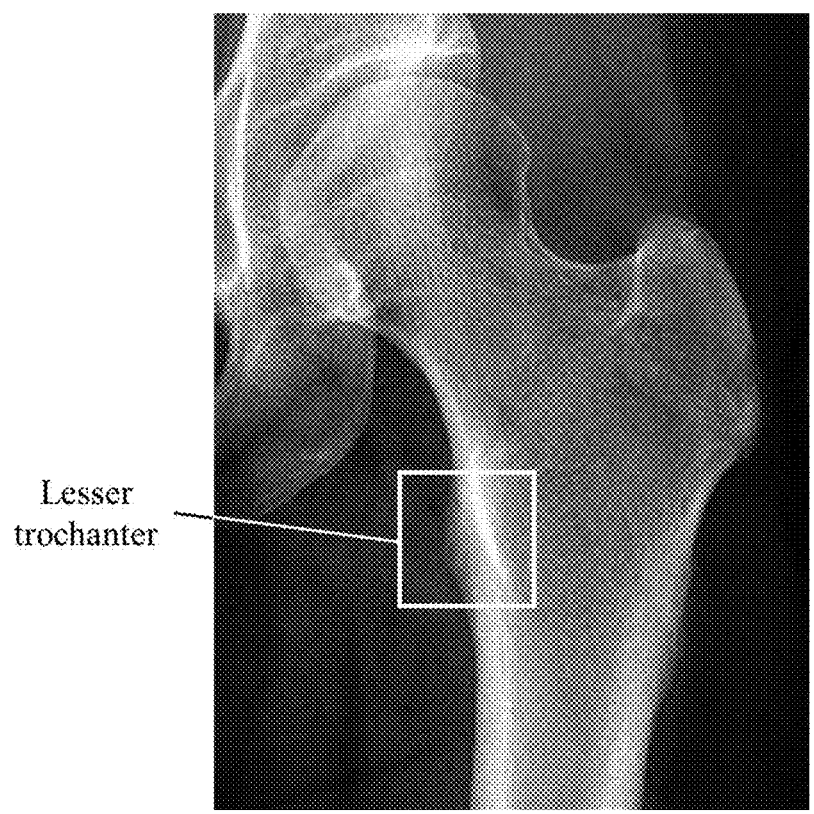
FIG. 5B is the enlarged image of the ROI shown in FIG. 5A

Cortical thickness index (CTI) is another widely used indicator to evaluate bone quality and osteoporosis. The cortical thickness index was defined as the ratio of cortical width minus endosteal width to cortical width at a level of 100 mm below the tip of the lesser trochanter (FIG. 5B shows the position of lesser trochanter). It is discovered that the cortical thickness of femur has positive correlation with BMD values of femoral neck, femoral shaft, greater trochanter, and total hip, as shown in FIG. 8A-8D. In CTI measurement, the AI detection model described above is trained to locate ROI of femur region below the tip of the lesser trochanter.

Figure 9:
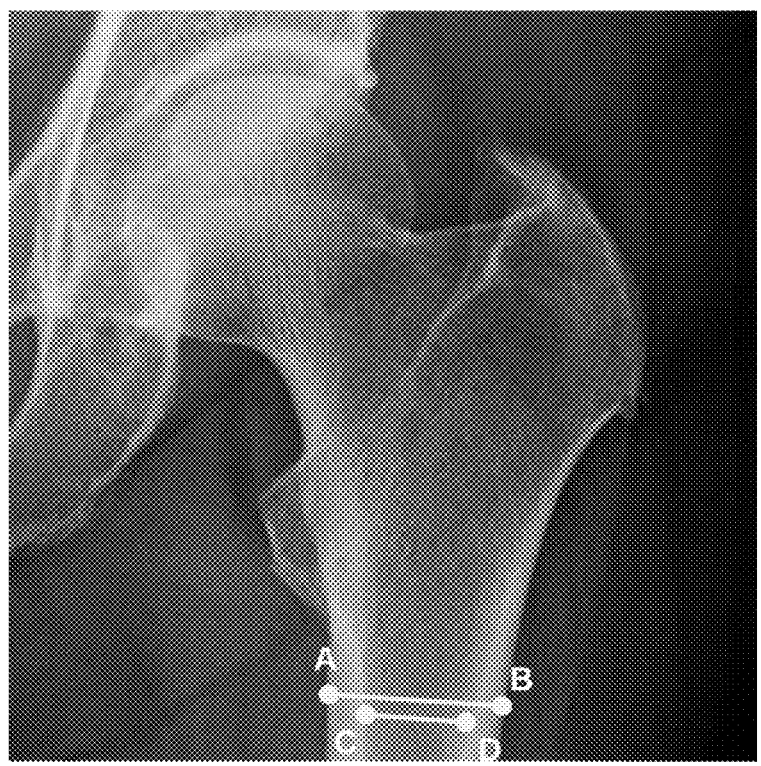
FIG. 9 shows the characteristic points corresponding to the outer and inner edges of the cortical bone used in calculation of CTI value.

In calculation of CTI from an X-ray image, a DNN model is trained to find the characteristic points corresponding to the outer and inner edges of the cortical bone, as shown in the landmark of A, B, C, and D in FIG. 9. The training method is as below:

(1) Preparing 153 hip joint X-ray images with characteristic points (i.e. points A, B, C, and D in FIG. 9) labeled by radiologists as training ground truth.
(2) Training High-Resolution Net (HRNet) algorithm to recognize the characteristic points.
(3) The trained AI model, which is a feature point detection model, can then be used to find the characteristic points in an input X-ray image.

The CTI value can thus be easily calculated by the equation: CTI=(AB−CD)/AB in percentage.

5. Texture Analysis

Since the strength of bones is influenced not only by the amount of bone but also by its geometrical distribution, the analyses of macro-/microstructural features are also important for evaluating the overall risk of fracture for a subject. A method of analyzing microstructure, texture analysis, is provided here.

Figure 10:
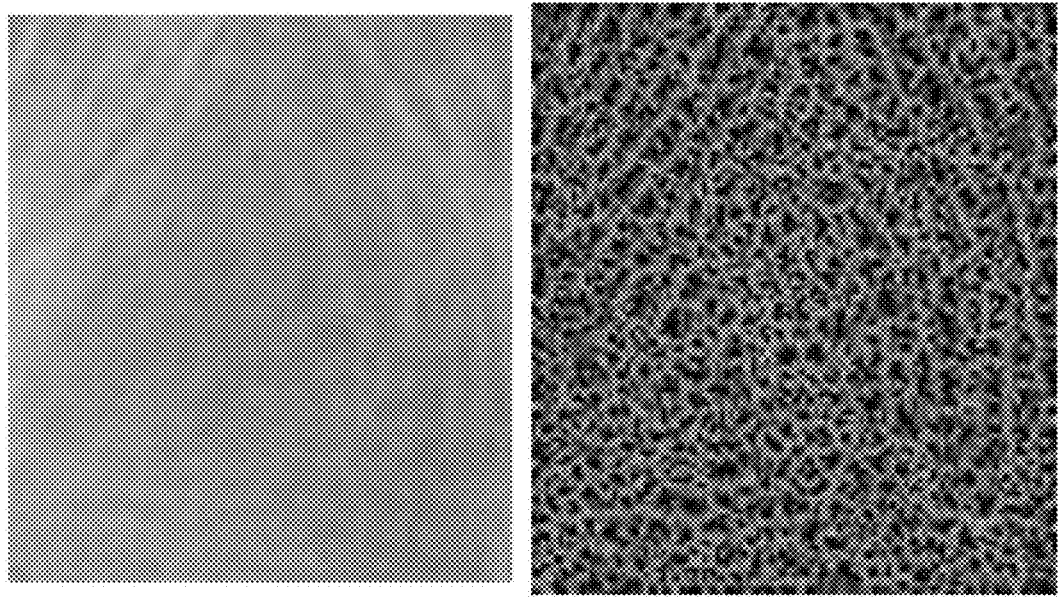
FIG. 10 shows an X-ray image before (left) and after (right) processed by local binary pattern (LBP) method.
Figure 11:
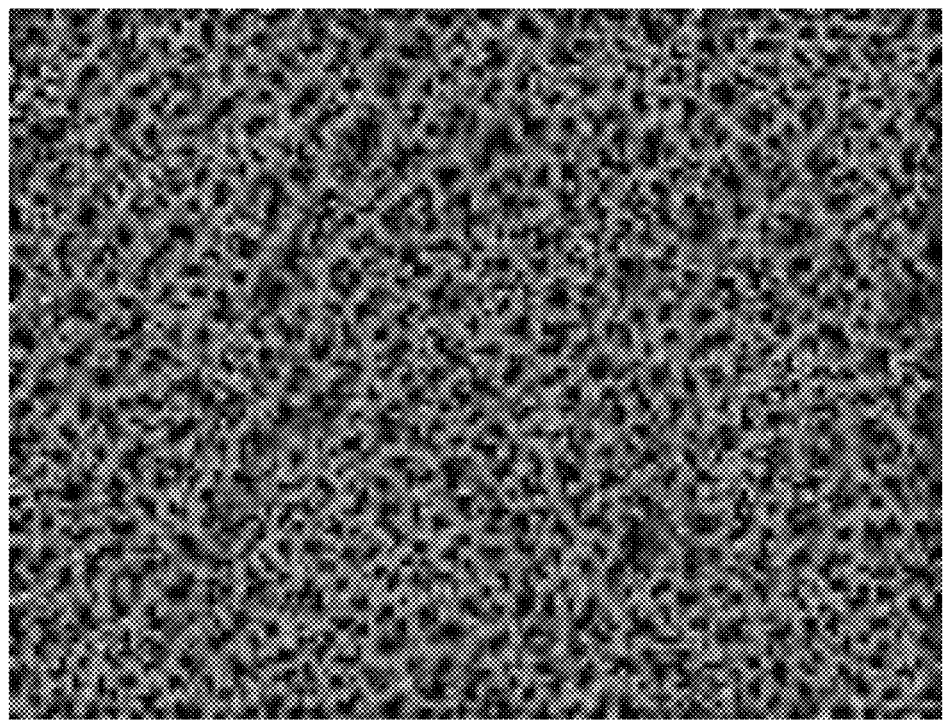
FIG. 11 shows the result of circle growing process applied by a region growing method. The grey circles in the image are the circles grown from the randomly chosen pixels.

The texture analysis analyzes hip regions and uses ROIs the same as which uses in BMD generation, i.e. regions of total hip, femoral neck, greater trochanter, and femoral shaft. With given ROIs, the local binary pattern (LBP) algorithm is performed on the ROIs to enhance local texture, as shown in FIG. 10. The region growing algorithm is then applied to LBP processed ROIs, in which the sponge-like structure is enhanced. There are many holes visible in the sponge-like structure of the LBP processed ROIs, and the region growing algorithm estimate the size distribution of radiuses of these holes. The workflow of the region growing algorithm is detailed below and as shown in FIG. 11.

(1) Randomly choose a pixel on the LBP processed image.
(2) From the chosen point, try to grow a circle from radius=1 to radius=9, and stop when half of the points on the perimeter of the circle are "WHITE" (brighter than a certain threshold)
(3) repeat step (1)-(2) N times. In this example N=100000, and FIG. 11 is the result of circle growing process.
(4) get histogram of the radius of fitted circles from r=1 pixel to r=9 pixels, where a pixel is around 66 μm. The region growing result of the ROI is {1:1290, 2:2487, 3:2267, 4:577, 5:73, 6:0, 7:0, 8:0, 9:0}, which can be plotted as a histogram.
(5) Repeat steps (1)-(4) 1000 times and average the histogram to smooth out the random fluctuations.

The histogram can tell the holes in the texture is dominated by larger radius or by smaller radius, as well as the distribution of the size of holes on the texture of the hip bone.

Figure 12:
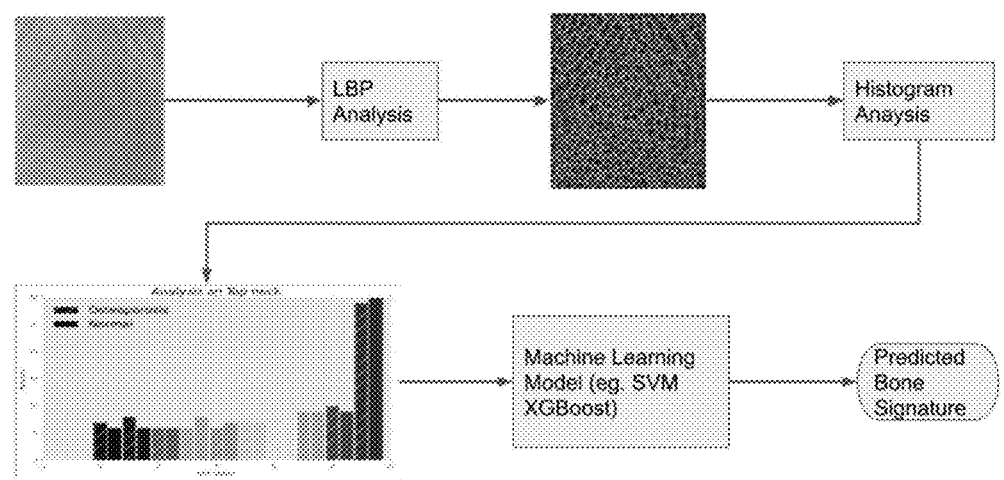
FIG. 12 is the workflow of texture analysis by LBP and region growing methods.
Figure 13A:
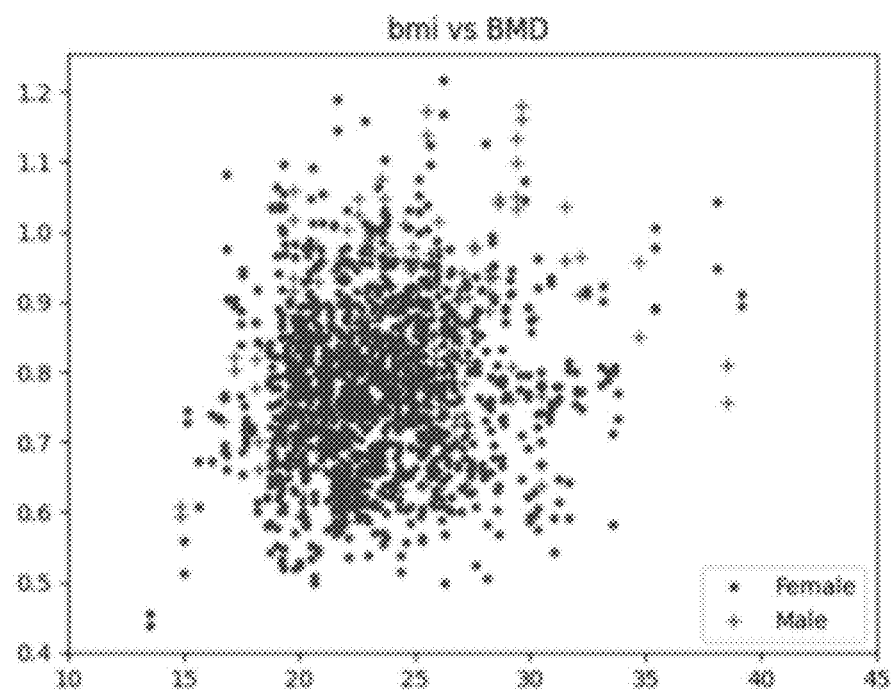
FIG. 13A shows the correlation between BMI values and measured BMD values.
Figure 13B:
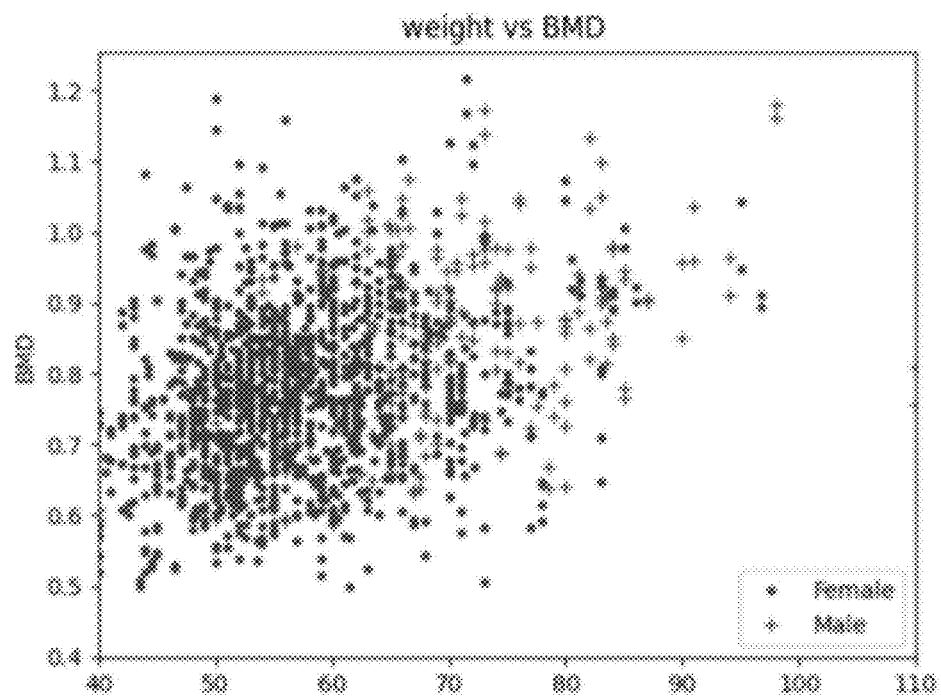
FIG. 13B shows the correlation between weight and measured BMD values.
Figure 13C:
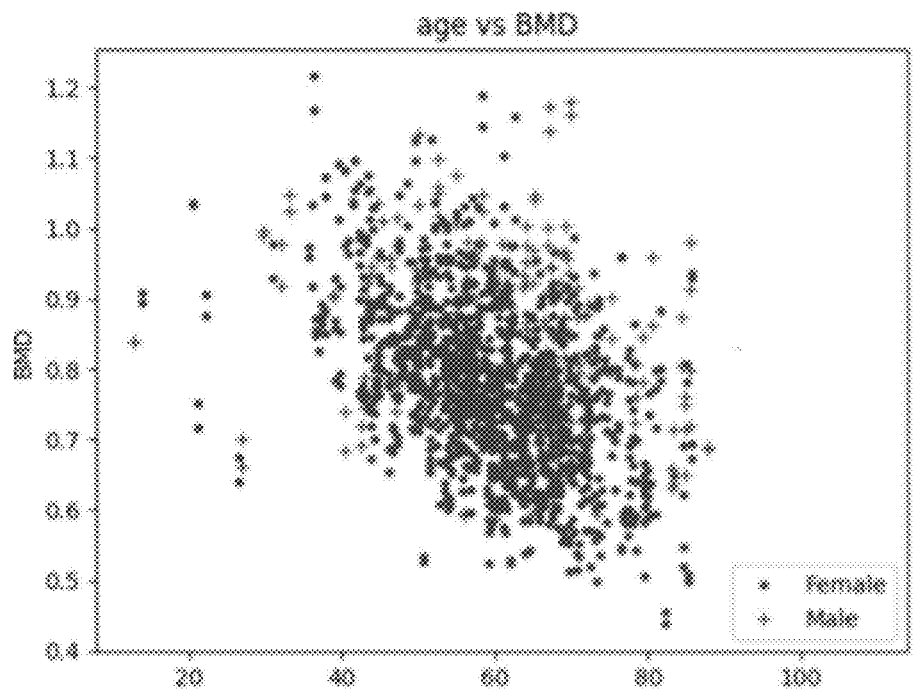
FIG. 13C shows the correlation between age and measured BMD values.
Figure 13D:
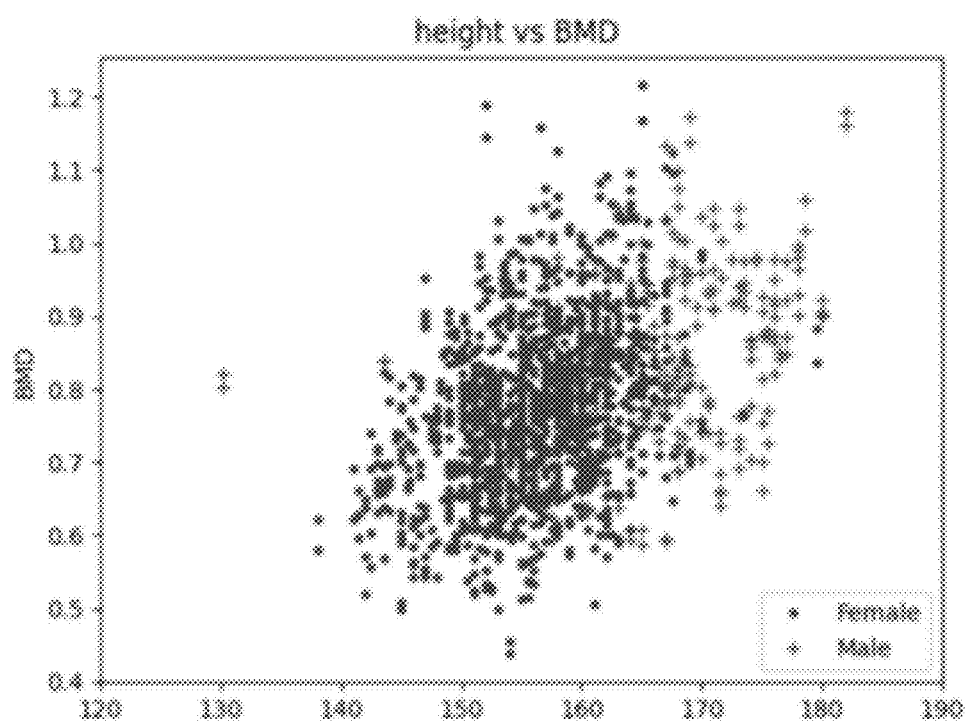
FIG. 13D shows the correlation between height and measured BMD values.

The above texture analysis method can be applied to both skeletal X-ray images of normal subjects and that of osteoporosis patients. The two groups of generated histograms can be used as the training dataset for machine learning. A workflow is provided in FIG. 12.

6. Bone Status Evaluation

A bone status of osteoporosis can be evaluated after obtaining generated BMD of the subject. Osteoporosis is diagnosed by the T-Score(s), which is converted from the BMD values. The classification standard defined by WHO, such as −2.5, −1, etc., indicates the status of osteoporosis of a subject. The diagnosis can be based on the lowest T-Score, or average T-Score. T-Score is the comparison value between the BMD examination results and the bone mineral density of healthy young people (WHO uses 25-year-old Caucasian woman as standard). A T-Score of −1 means one standard deviation below the average of healthy young people, and a T-Score of −2.5 means less than two and a half of standard deviations. Traditionally, osteoporosis is defined as with a T-score less than −2.5.

7. Application of Non-Image Features

Some health conditions which are not available from the X-ray image are closely related to osteoporosis, such as BMI, body weight, age, and height of a subject, as shown in FIG. 13A-FIG. 13D. Those non-image features can serve as additional input data for bone status evaluations by an AI. In the application of non-image features, the age, height, weight, and sex information of the subject is included in the training of AI model. The table below shows the comparison of the performance between models with or without additional non-image features:

TABLE 3

The performance of models with/without non-image features

| Model | AUC | Specificity when Sensitivity = 95% |
|---|---|---|
| X-ray image only, DNN model | 0.935 | 0.657 |
| X-ray image + non-image features, DNN model | 0.959 | 0.817 |

The above table clearly shows that the model employs additional non-image features outperformed the model utilizes image features only.

There are also other modified embodiments which may improve the performance of the generation of skeletal characteristic values and the evaluation of bone status. For example, for characteristic value generation (e.g. BMD generation), one or more regions of interest may also be used as the reference regions, where the reference regions are selected as characteristically stable regions. Those characteristically stable regions are usually regions where the bone density of which is less likely to change under the statistics of a large number of samples. Examples of stable regions include iliac crest of the pelvis and the subtrochanteric cortical bone of the femur. Another example of modified embodiment is using a reference object next to the bone subject (e.g. a phantom that provides a fixed density gradient as a fixed reference value for X-ray absorption and bone density estimation) to obtain an X-ray plane image including a reference luminance pattern. In this way, during the image processing, the reference luminance pattern is used to perform a calibration procedure, so that the X-ray images entering the image processing may have the same standard exposure intensity. Yet another modified embodiment is to perform a structural analysis of the trabeculae in the cancellous bone, where the estimated structural strength is correlated with a plurality of texture analysis results to evaluate the level of the osteoporosis and the risk of bone fracture.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter. Thus, it is intended that the present invention covers modifications and variations that come within the scope of the appended claims and their equivalents.

What is claimed is:

1. A method of generating one or more skeletal characteristic values (SCVs) of a subject from a planar bone image, comprising the steps of:
   identifying one or more regions of interest (ROIs) in the planar bone image; and
   performing one or more feature analyses on the regions of interest (ROIs) to generate the skeletal characteristic values (SCVs) comprising a plurality of density SCVs related to bone density;
wherein the planar bone image is a fixed angle projection image;
wherein the planar bone image does not include an image of a phantom with known densities; and
wherein the feature analyses comprise a density analysis performed by a trained machine learning model to generate the plurality of density SCVs from one of the ROIs.

2. The method of claim 1, before identifying the regions of interest further comprising:
   removing an interfering image caused by non-skeletal objects from the planar bone image.

3. The method of claim 1, after performing the feature analyses further comprising:
   determining one or more bone status of the subject based on the SCVs.

4. The method of claim 3, before determining the bone status of the subject further comprising introducing one or more non-image features of the subject, wherein the bone status is determined by the SCVs and the plurality of non-image features.

5. The method of claim 4, wherein the non-image features are selected from the group consisting of age, weight, height, and gender of the subject.

6. The method of claim 4, wherein the bone status is the Fracture Risk Assessment Tool (FRAX) score calculated by the generated SCVs and the non-image features.

7. The method of claim 1, wherein the regions of interest are identified by an AI trained by You Only Look Once (YOLO) algorithm.

8. The method of claim 1, wherein the density SCVs comprise bone mineral density (BMD) of different positions generated by the density analysis.

9. The method of claim 8, further comprising calculating T-scores from the generated BMD of the bones.

10. The method of claim 1, wherein the planar bone image comprises total hip region of the subject.

11. The method of claim 10, wherein one of the ROIs is region of a hip joint.

12. The method of claim 11, wherein the ROIs further comprise regions of femoral neck, greater trochanter and femoral shaft.

13. The method of claim 11, wherein the ROIs further comprise regions of iliac crest and subtrochanteric cortical bone.

14. The method of claim 1, wherein the feature analyses comprise a width analysis to obtain one or more width information of the bones in the ROIs.

15. The method of claim 14, wherein the planar bone image comprises total hip region of the subject, and the width analysis is performed by measuring the cortical width and the endosteal width of the lesser trochanter in the ROI.

16. The method of claim 15, wherein one of the SCVs is cortical thickness index (CTI) calculated based on the cortical width and the endosteal width of the lesser trochanter.

17. The method of claim 1, wherein the trained machine learning model is established with ResNet algorithm.

18. A method of generating one or more skeletal characteristic values (SCVs) of a subject from a planar bone image, comprising the steps of:
   identifying one or more regions of interest (ROIs) in the planar bone image; and
   performing one or more feature analyses on the regions of interest (ROIs) to generate the skeletal characteristic values (SCVs) comprising at least one texture SCV indicating the size distribution of the pores in the bone of the planar bone image; wherein:
the feature analyses comprise a texture analysis to generate the texture SCV;
the texture analysis comprises a local binary pattern (LBP) method and a region growing method; and
the region growing method is performed by calculating the number of pores with different porous sizes in an LBP processed ROI.

19. The method of claim 18, before identifying the regions of interest further comprising:
   removing an interfering image caused by non-skeletal objects from the planar bone image.

20. The method of claim 18, after performing the feature analyses further comprising:
   determining one or more bone status of the subject based on the SCVs.

21. The method of claim 20, before determining the bone status of the subject further comprising introducing one or more non-image features of the subject, wherein the bone status is determined by the SCVs and the plurality of non-image features.

22. The method of claim 21, wherein the non-image features are selected from the group consisting of age, weight, height, and gender of the subject.

23. The method of claim 18, wherein the regions of interest are identified by an AI trained by You Only Look Once (YOLO) algorithm.

24. The method of claim 18, wherein the calculation is performed by:
   randomly choosing a plurality of locations on the LBP processed ROI;
   determining the porous size of the pore at each of the locations;
   summing up the number of pores for each porous size to generate the texture SCV indicating the size distribution of the pores.

25. The method of claim 24, wherein porous size is determined by:
   growing a circle from a selected location with radii from small to large;
   determining the porous size of the pore at the selected location by identifying the radius where half of the points on the perimeter of the circle are brighter than a predetermined threshold.

26. A method of generating one or more skeletal characteristic values (SCVs) of a subject from a planar bone image, comprising the steps of:
   identifying one or more regions of interest (ROIs) in the planar bone image; and
   performing one or more feature analyses on the regions of interest (ROIs) to generate the skeletal characteristic values (SCVs) comprising a plurality of density SCVs related to bone density;
wherein the planar bone image is a fixed angle projection image;
wherein the feature analyses comprise a density analysis performed by a trained machine learning model to generate the plurality of density SCVs from one of the ROIs; and wherein the method does not include a step of removing an interfering image from the planar bone image.

27. The method of claim 26, after performing the feature analyses further comprising:
   determining one or more bone status of the subject based on the SCVs.

28. The method of claim 27, before determining the bone status of the subject further comprising introducing one or more non-image features of the subject, wherein the bone status is determined by the SCVs and the plurality of non-image features.

29. The method of claim 28, wherein the non-image features are selected from the group consisting of age, weight, height, and gender of the subject.

30. The method of claim 28, wherein the bone status is the Fracture Risk Assessment Tool (FRAX) score calculated by the generated SCVs and the non-image features.

31. The method of claim 26, wherein the regions of interest are identified by an AI trained by You Only Look Once (YOLO) algorithm.

32. The method of claim 26, wherein the density SCVs comprise bone mineral density (BMD) of different positions generated by the density analysis.

33. The method of claim 32, further comprising calculating T-scores from the generated BMD of the bones.

34. The method of claim 32, wherein the planar bone image further comprises images of one or more phantoms with known densities for bone density analysis.

35. The method of claim 26, wherein the planar bone image comprises total hip region of the subject.

36. The method of claim 35, wherein one of the ROIs is region of a hip joint.

37. The method of claim 36, wherein the ROIs further comprise regions of femoral neck, greater trochanter and femoral shaft.

38. The method of claim 36, wherein the ROIs further comprise regions of iliac crest and subtrochanteric cortical bone.

39. The method of claim 26, wherein the feature analyses comprise a width analysis to obtain one or more width information of the bones in the ROIs.

40. The method of claim 39, wherein the planar bone image comprises total hip region of the subject, and the width analysis is performed by measuring the cortical width and the endosteal width of the lesser trochanter in the ROI.

41. The method of claim 40, wherein one of the SCVs is cortical thickness index (CTI) calculated based on the cortical width and the endosteal width of the lesser trochanter.

42. The method of claim 26, wherein the trained machine learning model is established with ResNet algorithm.

* * * * *